US006673340B1

(12) United States Patent
Harrison et al.

(10) Patent No.: US 6,673,340 B1
(45) Date of Patent: Jan. 6, 2004

(54) BASEMENT MEMBRANE DEGRADING PROTEASES AS INSECT TOXINS AND METHODS OF USE FOR SAME

(75) Inventors: Robert L. Harrison, Ames, IA (US); Bryony C. Bonning, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/614,789

(22) Filed: Jul. 12, 2000

Related U.S. Application Data

(60) Provisional application No. 60/143,586, filed on Jul. 13, 1999.

(51) Int. Cl.[7] ........................ A01N 63/00; A61K 48/00; C12N 15/00; C12N 15/09; C12N 15/63

(52) U.S. Cl. ................... 424/93.2; 435/320.1; 435/348; 435/235.1; 536/23.5

(58) Field of Search ........................... 435/320.1, 235.1, 435/348; 536/23.5; 424/93.2

(56) References Cited

PUBLICATIONS

Bonning, Bryony C., et al., "Development of Recombinant Baculoviruses for Insect Control", 1996, *Anu. Rev. Entomol.* 41:191–210.

Engelhard, E.K., "The insect tracheal system: A conduit for the systemic spread of *Autographa californica M* nuclear polyhedrosis virus", 1994, *Proc. Natl. Acad. Sci. USA* 91:3224–3227.

Hess, Robert T., et al., "Temporal events in the invasion of the codling moth, *Cydia pomonella,* by a Granulosis, Virus: an electron microscope study", 1987, *J. of Invertebrate Pathology* 50:85–105.

Reddy, J.T., et al., "The size limited penetration of gold particles through insect basal laminae", 1990, *J. Insect Physiol.* 36(6):397–407.

Smith–Johannsen, Heidi, et al., "Infection of silkmoth follicular cells with *bombyx mori* nuclear–polyhedrosis virus", 1986, *J. of Intvertebrate Pathology* 48:78–84.

*Primary Examiner*—Peter Paras
(74) *Attorney, Agent, or Firm*—Greenlee Winner and Sullivan P.C.

(57) ABSTRACT

Novel insect toxins are disclosed for use in pesticidal compositions and methods. According to the invention basement membrane degrading proteases are identified which are capable of acting as insecticidal agents. Polynucleotides are provided which include expression constructs for the expression of the recombinant insecticidal proteases of the invention as recombinant insect pathogens, as well as transgenic plants with a substantial degree of insect resistance.

3 Claims, 4 Drawing Sheets

BASEMENT MEMBRANE DEGRADING PROTEASES AS INSECT TOXINS AND METHODS OF USE FOR SAME

CROSS-REFERENCE TO RELATED APPLICATIONS

This application claims the benefit of U.S. Provisional Application(s) No(s) 60,143,586 filed Jul. 13, 1999. +gi

GRANT REFERENCE

Work for this invention was funded in part by a grant from the United States Department of Agriculture, Agricultural Research Service Grant #97-35302-4325; USDA Project No. IOW03483. The Government may have certain rights in this invention.

FIELD OF THE INVENTION

This invention relates generally to the field of pest management for agriculture. More particularly the invention relates to the use of certain proteases as pesticidal toxins, particularly for transgenic insecticidal protocols. The invention further comprises insecticidal compositions as well as transgenic techniques including novel expression constructs, vectors, methods for the infection of insects and delivery of toxins, and ultimately for the development of insect resistant transgenic plants.

BACKGROUND OF THE INVENTION

One of the goals of agricultural research is to increase profitability of agriculture while decreasing its environmental impact. Integrated pest management programs need a diversity of control strategies and agents to maximize profits and minimize environmental damage. This need comes at a time when there has been a decrease in the diversity of classical pesticides. Although most experts agree that artificial pest control is needed to maintain our current level of agricultural productivity, over reliance on non selective pesticides has led to resistance, destruction of natural enemies, pest resurgence, and decreased profitability as well as environmental damage.

Synthetic chemical insecticides are effective for controlling pest insects in a wide variety of agricultural, urban, and public health situations. Unfortunately there are significant, often severe, side effects associated with the use of these products. Many pest populations have developed significant resistance to virtually all chemical insecticides, requiring higher and higher rates of usage for continued control. In a number of severe cases, highly resistant pest populations have developed which cannot be controlled by any available product. Chemical insecticides may also have deleterious effects on non-target organisms. Populations of beneficial arthropods, such as predators and parasites, are sometimes more severely affected by chemical applications than the pests themselves. Minor pests, ordinarily held in check by these beneficial organisms, may become serious pests when their natural constraints are removed by the use of chemical insecticides. Thus, new pest problems may be created by attempts to solve established problems.

Chemical insecticides may also have adverse effects on vertebrates. The use of DDT has been banned in the United States, due primarily to the insecticide's great environmental persistence and its resulting tendency to accumulate in the tissues of predatory birds, thereby disrupting their ability to produce viable eggs. The use of carbofuran has been severely restricted due to its avian toxicity, and many species of fish are known to be quite sensitive to a variety of insecticides. A number of insecticides, such as methyl parathion, are also quite toxic to humans and other mammals, and by accident or misuse have caused a number of human poisonings. Clearly, the field of insect control would benefit greatly from the discovery of insecticides with improved selectivity for insects and reduced effects on non-target organisms.

The problems described above, along with other concerns including the possibility that some insecticides may act as human carcinogens, have created a strong demand for the development of safer methods of insect control.

Insect pathogens have been the objects of much study as potential pest control agents. Generally, these pathogens are quite selective for insects and in many cases affect only a few closely related species of insects. A number of insect pathogens have been developed as products, including bacteria (e.g., *Bacillus thuringiensis* and *Bacillus popiliae*), viruses (e.g., nucleopolyhedroviruses) and protozoa (e.g., the microsporidian *Nosema locustae*). These products occupy only a small fraction of the insecticide market. Although pathogens may ultimately cause a high level of mortality in pest populations, the insects may take weeks to die and continue to feed for much of that time. Thus, an unacceptably high level of crop or commodity damage may be inflicted before control is achieved. Currently, researchers are actively seeking ways to improve the effectiveness of insect pathogens and other biological control tools.

Insecticidal toxins from arthropods have been the objects of increasing interest over the past decade. These materials have proved useful for the detailed study of neural and neuromuscular physiology in insects. They have also been used to enhance the effectiveness of certain insect pathogens. The insecticidal toxin AaIT, from the scorpion *Androctonus australis*, has been employed for both purposes. This toxin belongs to a group of peptides that are lethal to a variety of insects but have no detectable effect in humans. Other toxins in *A. australis* venom are lethal to mammals but have no effect on insects. Understanding the molecular basis of this selectivity may lead to the development of chemical insecticides with reduced effects on mammals and other non-target organisms.

A number of transgenic protocols have been employed to help reduce the environmental impact of non-selective pesticides. A summary of current protocols follows.

One method involves transformation of plants with plant disease resistance genes. Plant defenses are often activated by specific interaction between the product of a disease resistance gene (R) in the plant and the product of a corresponding avirulence (Avr) gene in the pathogen. A plant variety can be transformed with a cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (Arabidopsis RSP2 gene for resistance to *Pseudomonas syringae*).

The most extensively used heterologous gene for insect resistance involves the *Bt* endotoxin. A *Bacillus thuringiensis* protein, a derivative thereof or a synthetic polypeptide modeled thereon. See, for example, Geiser et al., *Gene* 48: 109 (1986), who disclose the cloning and nucleotide sequence of a *Bt* Delta-endotoxin gene. Moreover, DNA molecules encoding Detla-endotoxin genes can be purchased from American Type Culture Collection (Rockville, Md.), for example, under ATCC Accession Nos. 40098, 67136, 31995 and 31998.

Other examples include use of a lectin. See, for example, the disclosure by Van Damme et al., *Plant Molec. Biol.* 24: 25 (1994), who disclose the nucleotide sequences of several

*Clivia miniata* mannose-binding lectin genes, use of a vitamin-binding protein, such as avidin. See PCT application US93/06487 the contents of which are hereby incorporated by reference. (The application teaches the use of avidin and avidin homologues as larvicides against insect pests); and use of an enzyme inhibitor, for example, a protease inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor I), and Sumitani et al., *Biosci. Biotech. Biochem.* 57: 1243 (1993) (nucleotide sequence of *Streptomyces nitrosporeus* alpha-amylase inhibitor).

Still other recombinant strategies include use of insect-specific hormones or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

Further techniques include an insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

An enzyme involved in the modification, including the post-translational modification, of a biologically active molecule; for example, a chitinase, whether natural or synthetic has been used to create resistant transgenic plants. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hornworm chitinase, and Kawalleck et al., *Plant Molec. Biol.* 21: 673 (1993), who provide the nucleotide sequence of the parsley ubi4-2 polyubiquitin gene.

A molecule that stimulates signal transduction is yet another class of proteins. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

A hydrophobic mutant peptide has been used. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

A membrane permease, a channel former or a channel blocker has been used. For example, see the disclosure by Jaynes et al., *Plant Sci.* 89: 43 (1993), of heterologous expression of a cecropin lytic peptide analog to render transgenic tobacco plants resistant to *Pseudomonas solanacearum*.

Yet another technique includes a viral-invasive protein or a complex toxin-derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

An insect-specific antibody or an immunotoxin derived therefrom has been used. Thus, an antibody targeted to a critical metabolic function in the insect gut would inactivate an affected enzyme, killing the insect. C f. Taylor et al., Abstract #497, Seventh Int'l Symposium on Molecular Plant-Microbe Interactions (Edinburgh, Scotland, 1994) (enzymatic inactivation in transgenic tobacco via production of single-chain antibody fragments).

Finally, a virus-specific antibody has been shown to confer protection. See, for example, Tavladoraki et al., *Nature* 366: 469 (1993), who show that transgenic plants expressing recombinant antibody genes are protected from virus attack.

As can be seen from the foregoing there is a continuing need for environmentally safe alternatives to chemical pesticides.

It is an object of the present invention to provide genetically engineered insect pathogens which express a novel toxin.

It is yet another object of the invention to provide transgenic plants which express a non specific insect toxin to engineer insect resistant plants.

It is yet another object to provide expression constructs, vectors, and protocols for providing the insect pathogen and transgenic plants of the invention.

Other objects of the invention will become apparent from the detailed description of the invention which follows.

SUMMARY OF THE INVENTION

According to the invention, applicants have discovered that proteases which degrade or disrupt basement membranes such as metalloproteases, collagenases, gelatinases, stromelysins, cysteine proteases, as well as basement degrading proteases from snake venom, invertebrates, fungi, and bacteria are useful as insecticidal toxins. Surprisingly applicants have discovered that the basement membrane degrading proteases themselves act as toxins and may be used as insecticidal agents with efficacy against a variety of pest species.

When produced within insect tissues the protease is exported from the cells and degrades the basement membrane surrounding the tissues. Basement membranes provide structural support, a filtration function and a surface for cell attachment, migration and differentiation. Degradation of the basement membrane results in rapid death of the insect.

According to the invention polynucleotides are provided which include expression constructs for the expression of recombinant insecticidal proteases in insect pathogens or in transgenic plants. The expression constructs may comprise regulatory elements such as promoters and termination signals which are effective in the particular host cell or recipient (pathogen or plant) of the construct.

For purposes of this application the following terms shall have the definitions recited herein. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. The terms defined below are more fully defined by reference to the specification as a whole.

As used herein the term "basement membrane degrading protease" shall include any protease capable of digesting or otherwise disrupting the basement membrane of a desired pest. This includes but is not limited to:

Mammalian matrix metalloproteases (MMPs) including:
Collagenases: (Interstitial collagenase (MMP-1, fibroblast collagenase, EC 3.4.24.7) Collagenase-3 (MMP-13) *Neutrophil collagenase* (MMP-5, EC 3.4.24.34) PMN-type collagenase (MMP-8);
Gelatinases(Gelatinase A (MMP-2, 72 kDa type IV collagenase, EC 3.4.24.24); Gelatinase B (MMP-9, 92 kDa type IV collagenase, EC 3.4.24.35))
Stromelysins: (Stromelysin-1 (MMP-3, transin, proteoglycanase, EC 3.4.24.17); Stromelysin-2 (MMP-10, transin-2, EC 3.4.24.22), Stromelysin-3 (MMP-11), Matrilysin (MMP-7, pump-1, EC 3.4.24.23); Metalloelastase (MMP-12); membrane-type MMP (MMP-14)
Mammalian cysteine proteases, including Cathepsin B (EC 3.4.22.1), Cathepsin L (EC 3.4.22.15), Cathepsin N
Snake venom proteases, including, Crotalus atrox (Western diamondback rattlesnake) and hemorrhagic metalloproteinases: (Ht-a, Ht-c, Ht-d, and Ht-e)
Invertebrate proteases, including: *Hypoderma lineatum* (fly) collagenase (EC 3.4.21.49), Uca pugilator (crab) collagenolytic endopeptidase (EC 3.4.21.32),
Fungal proteases, such as *Entomophthora collagenase* (EC 3.4.21.33)
Bacterial proteases, including:*Clostridium histolyticum collagenase* (EC 3.4.24.03), *Streptomyces collagenase, Serratia marcescens cysteine endopeptidase.*

The term is also intended to include conservatively modified variants and other peptide variants which retain enzymatic activity of such proteases. The nucleotide sequences encoding these enzymes are generally known to those of skill in the art and available through sources such as Genbank. (see fibroblast collagenase, EC3.4.24.7 Genbank accession number X05231, PMN-type collagenase (MMP-8) Genbank accession number J05556, Gelatinase B (MMP-9, 92 kDa type IV collagenase, EC3.4.24.35 Genbank accession number J05070, Stromelysin-1 (MMP-3, transin, proteoglycanase, EC 3.4.24.17 Genbank accession number X05232), Stromelysin-2 (MMP-10, transin-2, EC 3.4.24.22, Genbank accession number X07820), Matrilysin (MMP-7, pump-1, EC 3.4.24.23 Genbank accession number X07819), Metalloelastase (MMP-12) Genbank accession number L23808, Cathepsin B (EC 3.4.22.1) Genbank accession number M14221, Cathepsin L (EC 3.4.22.15) Genbank accession number L23808, Crotalus atrox (Western diamondback rattlesnake) hemorrhagic metalloproteinases: Ht-a, Ht-c, Ht-d, and Ht-e Accession numbers:Ht-a: U01234, Ht-c: U01236, Ht-d: U01237, Uca pugilator (crab) collagenolytic endopeptidase (EC 3.4.21.32) Genbank accession number U49931 (accession # for the Uca enzyme), and Clostridium histolyticum collagenase (EC 3.4.24.03) Genbank accession number D29981. Those of skill in the art will appreciate that other basement membrane degrading proteases will be applicable to the teachings herein, or will become available or isolated using no more than routine experimentation.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). See also, Creighton (1984) Proteins W. H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477–498 (1989)). Thus, the maize preferred codon for a particular amino acid may be derived from known gene sequences from maize. Maize codon usage for 28 genes from maize plants are listed in Table 4 of Murray et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells or insect cells.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "nucleic acid" or "nucleotide" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" can include reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. Particularly preferred plants are agricultural plants.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as Agrobacterium or Rhizobium. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, underexpressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

A "structural gene" is a DNA sequence that is transcribed into messenger RNA (mRNA) which is then translated into a sequence of amino acids characteristic of a specific polypeptide.

The term "expression" refers to biosynthesis of a gene product. Structural gene expression involves transcription of the structural gene into mRNA and then translation of the mRNA into one or more polypeptides.

A "cloning vector" is a DNA molecule such as a plasmid, cosmid, or bacterial phage that has the capability of replicating autonomously in a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance or ampicillin resistance.

An "expression vector" is a DNA molecule comprising a gene that is expressed in a host cell. Typically, gene expression is placed under the control of certain regulatory elements including promoters, tissue specific regulatory elements, and enhancers. Such a gene is said to be "operably linked to" the regulatory elements.

A "recombinant host" may be any prokaryotic or eukaryotic cell that contains either a cloning vector or an expression vector. This term also includes those prokaryotic or eukaryotic cells that have been genetically engineered to contain the cloned genes in the chromosome or genome of the host cell.

A "transgenic plant" is a plant having one or more plant cells that contain an expression vector. Plant tissue includes differentiated and undifferentiated tissues or plants, including but not limited to roots, stems, shoots, leaves, pollen, seeds, tumor tissue, and various forms of cells and culture such as single cells, protoplasm, embryos, and callus tissue. The plant tissue may be in plant or in organ, tissue, or cell culture. These proteins can be used in techniques described herein as molecular markers in breeding to identify and/or select plants with improved insect resistance.

As used herein the term "substantially resistant" refers to the fact that the transformed and transgenic plants of this invention have resistance to pests that invade, infect, or consume the particular plant species when compared to the corresponding non-transgenic or non-transformed plant.

DETAILED DESCRIPTION OF THE INVENTION

Figure 1:
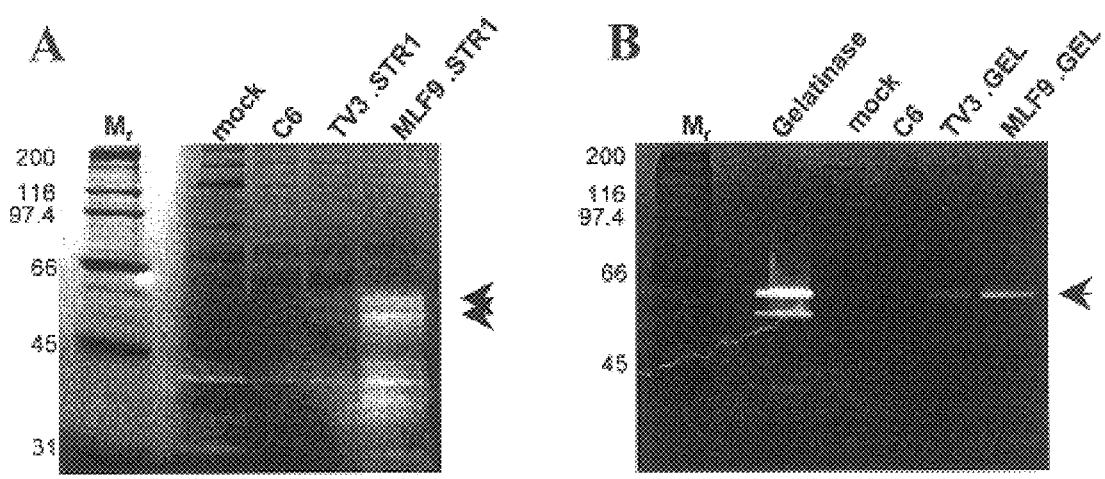
FIG. 1. Zymography of proteases expressed by recombinant *Autographa californica* multicapsid nucleopolyhedroviruses. (A) Casein zymography of medium from mock-infected High Five cells (mock) and cells infected with wild-type AcMNPV (C6) and recombinant AcMNPV expressing rat stromelysin-1 (TV3.STR1, MLF9.STR1). (B) Gelatin zymography of medium from mock- and wild-type virus-infected cells and cells infected with human gelatinase A-expressing viruses (TV3.GEL, MLF9.GEL). Gelatinase: 0.5 U of purified human gelatinase A (Boehringer Mannheim). Recombinant virus-specific bands are indicated by arrows in both zymographs. Molecular mass markers ($M_r$) are indicated in kDa.

Toxins currently used for insecticidal compositions such as the *Bt* toxin act at the gut level. The toxins of the invention provide a novel mechanism of action from within the hemocoel of the insect. See for example, National Application No. WO99/US21123, WO2000/15758 Miller et al. These toxins are expected to be active against a variety of pest species (unlike *Bt* toxins) and will provide a valuable strategy for control of pests for which transgenic approaches are not currently available.

Various toxins derived from scorpion venom are also currently used in insecticidal strategies and have been shown to be active in the hemocoel, but these toxins target the nerves and must accumulate to sufficient levels before resulting in toxicity. The protease toxins of the invention are active as soon as they are exported from the insect tissue.

Basement membranes (BMs) are extracellular layers of protein that surround all animal tissues, providing structural support, a filtration function, and a surface for cell attachment, migration, and differentiation (Yurchenco, P. D., and O'Rear, J. 1993.Supramolecular organization of basement membranes. In "Molecular and Cellular Aspects of Basement Membranes" (D. H. Rohrbach, and R. Timpl, Eds.), pp. 19–47. Academic Press, New York). BMs consist mostly of type IV collagen, laminin, and proteoglycans. The major components of BMs are conserved among vertebrates and invertebrates (Fessler, J. H., and Fessler, L. I. 1989. Drosophila extracellular matrix. *Annu. Rev. Cell. Biol.* 5, 309–339; Pedersen, K. J. 1991.Structure and composition of basement membranes and of the basal matrix systems in selected invertebrates. *Acta Zool.* 72, 181–201; Ryerse, J. S. 1998. Basal Laminae. In "Insecta" (F. W. Harrison, and M. Locke, Eds.), Vol. 11A, pp. 3–16. Wiley-Liss, Inc., New York).

The invention is applicable to insect control in general, including but not limited to the Noctuidae. This family includes some of the most destructive agricultural pests including the European corn borer, armyworms and cutworms. The technology may also be applied to a variety of other pests in Iowa including stalk borers, sod web worm, hop vine borer and soybean loopers.

Polynucleotides encoding the toxins may be introduced into a suitable vector (either live or attenuated). When an insect cell is the host the vector will traditionally be an insect pathogen such as *Bacillus thuringiensis, Bacillus popiliae*, a nucleopolyhedroviruses (Baculovirus) or microsporidian and applied to the sites of the pest to be controlled, where the live host will proliferate and be ingested by the pest according to methods known in the art and exemplified herein (see also, for example U.S. Pat. No. 5,135,867 for such methods employing the *Bt* toxin, or U.S. Pat. No. 5,874,298 for methods employing insecticidal toxins from wasp) or the toxins may be used to create transgenic organisms for production and harvesting of the recombinant protein in bacterial cells, for topically applied insecticides or finally to create insect resistant transgenic plants expressing the toxins. For creation of transgenic plants a preferred delivery system would be one which will deliver the toxins to the hemocoel of the insect.

The invention further comprises expression cassettes comprising a promoter, nucleotide sequence comprising a basement membrane degrading toxin gene, the expression of which is desired in a plant or microbial cell, and a polyadenylation or stop signal. The expression cassette can be encompassed in plasmid or viral vectors for transformation of plant protoplast or microbial cells.

The invention also encompasses transformed bacterial cells for maintenance and replication of the vector or for production and harvesting of the protease toxins, as well as transformed monocot or dicot cells and ultimately transgenic plants, and breeding materials developed from the transgenic plants.

In a preferred embodiment the microbial host is a Baculovirus. Baculoviruses are arthropod-specific pathogens which infect a large number of insect pests in the order Lepidoptera (Adams, J. R., and McClintock, J. T. 1991. Baculoviridae. Nuclear polyhedrosis viruses, part 1: Nuclear polyhedrosis viruses of insects. In "Atlas of Invertebrate Viruses" (J. R. Adams, and J. R. Bonami, Eds.), pp. 87–204. CRC Press, Boca Raton, Fla. Because baculoviruses are environmentally benign and do not infect vertebrates, they have been the subject of intensive study as possible alternatives or supplements to chemical insecticides (Black, B. C., et al., 1997. Commercialization of baculoviral insecticides. In "*The Baculoviruses*" (L. K. Miller, Ed.), pp. 341–387. Plenum Press, New York; Moscardi, F. 1999. Assessment of the application of baculoviruses for control of Lepidoptera. *Annu. Rev. Entomol.* 44, 257–289). Baculoviruses possess double-stranded circular DNA genomes contained within enveloped, rod-shaped virions. Virions are enclosed within a protective crystalline matrix consisting of the viral protein polyhedrin to form polyhedra. Polyhedra can be applied for insect control by using conventional insecticidal application techniques. Primary infection of the host insect is initiated when larvae ingest polyhedra. The polyhedrin crystalline matrix dissolves in the alkaline environment of the midgut, releasing virions that infect the midgut cells. Progeny virus from this primary infection establish secondary infection of other tissues within the host. After viral gene expression, DNA replication, and virion assembly, polyhedra are produced in massive quantities in the tissues of the host. When the host dies from infection, the cadaver lyses and releases polyhedra into the environment to initiate further rounds of infection.

Recombinant baculoviruses expressing genes that encode a variety of insect-selective toxins or development-disrupting enzymes and hormones have been shown to kill insects faster and reduce feeding damage to a greater extent than wild-type baculoviruses (van Beek, N. A. M., and Hughes, P. R. 1998. The response time of insect larvae infected with recombinant baculoviruses. *J. Invertebr. Pathol.* 72, 338–347; Harrison, R. L., and Bonning, B. C. 2000. Use of scorpion neurotoxins to improve the insecticidal activity of Rachiplusia ou multicapsid nucleopolyhedrovirus. *Biol. Control* 17, 191–201).

According to the invention, a recombinant baculovirus *Autographa californica* multicapsid nucleopolyhedroviruses (AcMNPV) that expresses proteases known to digest BM proteins were constructed. Viruses that express rat stromelysin-1 (EC 3.4.24.17, matrix metalloprotease-3), human gelatinase A (EC 3.4.24.24, matrix metalloprotease-2), or a cathepsin L (EC 3.4.22.15) from the flesh fly, *Sarcophaga peregrina* Robineau-Desvoidy, were produced and tested for reduced survival time of AcMNPV-infected *Heliothis virescens* Fabricius. The *S. peregrina* cathepsin L significantly reduced survival time and feeding damage caused by infected larvae.

MOLECULAR BIOLOGY TECHNIQUES

The following is a non-limiting general overview of Molecular biology techniques which may be used in performing the methods of the invention. Those of skill in the art will appreciate that the selection of suitable expedients such as promoter selection, vector type and transformation techniques comprises a number of alternatives available to those of skill in the art and will vary according to the host cell used. The selection of the same for optimization of parameters for the novel insecticidal strategies herein involve no more than routine experimentation. A comprehensive review of Baculovirus techniques is disclosed in (King, L. A., et al., 1992, The Baculovirus Expression System, London: Chapman & Hall. 229 pp.; O'Reilly, D. R., et al., 1992, *Baculovirus Expression Vectors—a Laboratory Manual*. New York: Freeman. 347 pp.).

Genetic Engineering of Baculoviruses

The aim of genetic engineering of baculoviruses for use as insecticides is to combine the pathogenicity of the virus with the insecticidal action of a toxin, hormone, or enzyme. Upon infection of the insect larva with the recombinant baculovirus, the foreign protein is expressed. If this protein is toxic to the insect, the insect will die rapidly from this effect, rather than from the viral infection itself. The recombinant approach will probably also be used to improve production, modify host range, and enhance the utility of various insect viruses as biopesticides. However, the goal of the research reviewed here is to reduce the time from infection with the recombinant virus to death of the insect such that feeding damage is below the economic threshold. This goal necessitates an approximate lethal-time ratio (lethal time of test virus divided by lethal time of wild-type virus) (Bonning et al., 1993, "Lethal ratios: an optimized strategy for presentation of bioassay data generated from genetically engineered baculoviruses, *J. Invert. Pathol.* 62:196–97) of 0.4–0.5 for control of insect pests on many crops. Reduction of the lethal time may also enhance farmer or use acceptance of baculovirus insecticides.

Two major baculovirus-expression systems have been developed for the production of recombinant proteins for research and clinical use. These are based on the nucleopolyhedrovirus derived from the alfalfa looper, *Autographa californica* (AcNPV), and a similar virus from the silkworm, *Bombyx mori* (BmNPV). The sequences of the entire genomes of both AcNPV and BmNPV have now been determined (Ayres, M. D., et al., 1994, "The complete sequence of *Autographa californica* nuclear polyhedrosis virus", *Virology* 202:586–605; Gomi, S., et al., 1999, "Sequence analysis of the genome of *Bombyx mori* nucleopolyhedrovirus", *J. Gen. Virl.* 80:1323–1337). Early engineering work was carried out with BmNPV for high levels of protein production in larvae of *B. mori*. As *B. mori* is the only known host for BmNPV, this approach also provided biological containment for the virus. Most recent work in developing the virus for insect control has concentrated on AcNPV. A variety of recently developed techniques and transfer vectors greatly facilitate the engineering process (Bishop, D H L, 1992, "Baculovirus expression vectors", *Sem. Virol.* 3:253–64; Davies, A. H., 1994, "Current methods for manipulating baculoviruses", *Biotechnology* 12:47–50; Luckow, V. A., 1994, "Insect cell expression technology. In *Principles and Practice of Protein Engineering*, ed. J L Cleland, C S Craik, pp. 1–27. New York: Wiley & Sons). Protein-expression systems have also been established in other baculoviruses, such as *Helicoverpa zea* NPV (Corsaro, B. G., et al., 1989, "Transfection of cloned *Heliothis zea* cell lines with the DNA genome of the *Heliothis zea* nuclear polyhedrosis virus", *J. Virol. Methods* 25:283–91) and *Lymantria dispar* NPV (Yu, Z., et al., 1992, "Genetic engineering of a *Lymantria dispar* nuclear polyhedrosis virus for expression of foreign genes", J. Gen. Virol. 73:1509–14; Harrison, R. L., et al., 2000, "Use of scorpion neurotoxins to improve the insecticidal activity of Rachiplusia ou multicapsid nucleopolyhedrovirus", *Biol. Control*, 27(3):292–302). This research provides the basis for engineering of these viruses for use as insect pest-control agents in the future.

The circular genome of AcNPV is approximately 134 kilobase pairs (kb) (Ayres, M. C., et al., 1994, supra). Because of the difficulty of direct manipulation of such a large piece of DNA, engineering of a baculovirus is usually carried out in two steps. First, the foreign gene is incorporated into a baculovirus-transfer vector. Most transfer vectors used are bacterial plasmid, University of California (pUC), derivatives, which encode an origin of replication for propagation in *Escherichia coli* and an ampicillin-resistance gene. The pUC fragment is ligated to a small segment of DNA taken from the viral genome. The foreign gene sequence is incorporated into a cloning site downstream of the promoter selected to drive expression. For the second step, the transfer vector is mixed with DNA from the parental virus. The engineered DNA is incorporated into the virus via homologous recombination events within the nucleus of cultured insect cells. Unlike genetic engineering in plants, which results in a rather random incorporation of new DNA into the genome, the baculovirus system allows the precise insertion of foreign DNA without disruption of other genes. No drug-resistance markers are included in the final clone, which eliminates some of the major objections raised to recombinant organisms (Fox, J. L., 1995, "EPA's first commercial release is still pending", *Biotechnology* 13:114–15). Commercial kits and reagents are available for this work, as well as several excellent manuals (King, L. A., et al., 1992, *The Baculovirus Expression System*, London: Chapman & Hall. 229 pp.; O'Reilly, D. R., et al., 1992,

*Baculovirus Expression Vectors*—a Laboratory Manual. New York: Freeman. 347 pp.). A number of recently developed alternative approaches for genetic engineering of baculoviruses have been reviewed elsewhere (Davies, A. H., 1994, supra).

Early research involved engineering of these viruses for use as protein-expression vectors rather than for insect control (Smith, G. E., et al., 1983, "Production of human β-interferon in insect cells infected with a baculovirus expression vector", *Mol. Cell. Biol.* 3:2156–65). The approach involved replacing the gene encoding polyhedrin with the foreign gene of interest. Expression of the foreign gene was driven by the polyhedrin promoter in a polyhedrin-negative virus. Although these viruses can be manipulated successfully in cell culture for production of high levels of foreign protein, they lose any advantage conferred by the polyhedrin coat that protects the virus from inactivation by desiccation under field conditions. Replacement of the viral gene encoding the p10 protein (Vlak, J. M., et al., 1990, "Expression of a cauliflower mosaic virus gene I using a baculovirus vector based on the p10 gene and a novel selection method", *Virology* 178:312–20), which is involved in calyx attachment and nuclear lysis, also resulted in reduced viral fitness. The stability of polyhedra produced by p10-negative viruses is greatly reduced (Williams, G. V., et al., 1989, "A cytopathological investigation of *Autographa californica* nuclear polyhedrosis virus p10 gene function using insertion/deletion mutants", *J. Gen. Virol.* 70:187–202).

An alternate approach to replacement of a viral gene with a foreign gene sequence is to duplicate a viral promoter. In this instance, none of the viral genes are lost, and promoters of essential viral genes can be used for expression of foreign proteins. The level and timing of expression of a particular protein by a recombinant baculovirus is determined in part by the promoter chosen to drive transcription of the foreign gene sequence. Currently, the polyhedrin and p10 promoters are used most frequently for expression of recombinant proteins. However, expression under the basic protein promoter was higher in several instances (Bonning, B. C., et al., 1994, "Superior expression of juvenile hormone esterase and β-galactosidease from the basic protein promoter of *Autographa californica* nuclear polyhedrosis virus compared to the p10 protein and polyhedrin promoters", *J. Gen. Virol.* 75:1551–56; Lawrie, A. M., et al., 1993, *Baculovirus expression of urokinase-type plasminogen activator: comparison of late and very late promoters*. Presented at Annu. Meet. Am. Soc. Virol. 12$^{th}$, Davis Calif.; Sridhar, P., et al., 1993, "Temporal nature of the promoter and not the relative strength determines the expression of an extensively processed protein in a baculovirus system", *FEBS Lett.* 315:282–86; Lu, A., et al., 1996, "Signal Sequence and Promoter Effects on the Efficacy of Toxin-Expressing Baculoviruses as Biopesticides" *Biological control: theory and applications*, 7:320). In the future, the use of early promoters, hybrid promoters, and promoters from other species will increase, particularly with the identification of peptides and proteins that disrupt insect biology at lower expression levels.

As mentioned earlier, the application is not limited to Baculovirus as the insect pathogen, other insect pathogens may also be used such as Bacillus and other pathogens listed herein and transformation techniques with respect to the same are discussed in detail in the documents incorporated herein by reference.

The following is a summary of molecular biology techniques with an emphasis on plant transformation.

STRUCTURAL GENE

The insect toxin encoding nucleotide sequence may be used itself or paired with other structural genes or polynucleotides the expression of which is desired in a particular cell.

PROMOTERS

Promoters selected may be constitutive, inducible, or tissue specific and may be used in conjunction with naturally occurring flanking coding or transcribed sequences of the desired structural gene/s or with any other coding or transcribed sequence that is critical to structural gene formation and/or function.

It may also be desirable to include some intron sequences in the promoter constructs since the inclusion of intron sequences in the coding region may result in enhanced expression and specificity.

Additionally, regions of one promoter may be joined to regions from a different promoter in order to obtain the desired promoter activity resulting in a chimeric promoter. Synthetic promoters which regulate gene expression may also be used.

The expression system may be further optimized by employing supplemental elements such as transcription terminators and/or enhancer elements.

A large number of suitable promoter systems are available. For example one constitutive promoter useful for the invention is the cauliflower mosaic virus (CaMV) 35S. It has been shown to be highly active in many plant organs and during many stages of development when integrated into the genome of transgenic plants including tobacco and petunia, and has been shown to confer expression in protoplasts of both dicots and monocots.

Organ-specific promoters are also well known. For example, the E8 promoter is only transcriptionally activated during tomato fruit ripening, and can be used to target gene expression in ripening tomato fruit (Deikman and Fischer, *EMBO J.* (1988) 7:3315; Giovannoni et al., *The Plant Cell* (1989) 1:53). The activity of the E8 promoter is not limited to tomato fruit, but is thought to be compatible with any system wherein ethylene activates biological processes. Similarly the Lipoxegenase ("the LOX gene") is a fruit specific promoter.

Root specific promoters include the Cam 35 S promoter disclosed in U.S. Pat. No. 391,725 to Coruzzi et al; the RB7 promoter disclosed in U.S. Pat. No. 5,459,252 to Conking et al and the promoter isolated from *Brassica napus* disclosed in U.S. Pat. No. 5,401,836 to Bazczynski et al. which give root specific expression.

Another important method that can be used to identify cell type specific promoters that allow even to identification of genes expressed in a single cell is enhancer detection (O'Kane, C., and Gehring, W. J. (1987), "Detection in situ of genomic regulatory elements in Drosophila", *Proc. Natl. Acad. Sci. USA*, 84, 9123–9127). This method was first developed in Drosophila and rapidly adapted to mice and plants (Wilson, C., Pearson, R. K., Bellen, H. J., O'Kane, C. J., Grossniklaus, U., and Gehring, W. J. (1989), "P-element-mediated enhancer detection: an efficient method for isolating and characterizing developmentally regulated genes in Drosophila", *Genes & Dev.*, 3, 1301–1313; Skarnes, W. C. (1990), "Entrapment vectors: a new tool for mammalian genetics", *Biotechnology*, 8, 827–831; Topping, J. F., Wei, W., and Lindsey, K. (1991), "Functional tagging of regulatory elements in the plant genome", *Development,* 112, 1009–1019; Sundaresan, V., Springer, P. S., Volpe, T., Haward, S., Jones, J. D. G., Dean, C., Ma, H., and Martienssen, R. A., (1995), "Patterns of gene action in plant development revealed by enhancer trap and gene trap transposable elements", *Genes & Dev.*, 9, 1797–1810).

The promoter used in the method of the invention may be an inducible promoter. An inducible promoter is a promoter that is capable of directly or indirectly activating transcription of a DNA sequence in response to an inducer. In the absence of an inducer, the DNA sequence will not be transcribed. Typically, the protein factor that binds specifically to an inducible promoter to activate transcription is present in an inactive form which is then directly or indirectly converted to the active form by the inducer. The inducer may be a chemical agent such as a protein, metabolite (sugar, alcohol etc.), a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating, or similar methods. Examples of inducible promoters include the inducible 70 kd heat shock promoter of D. melanogaster (Freeling, M., Bennet, D. C., Maize ADN 1, *Ann. Rev. of Genetics*, 19:297–323) and the alcohol dehydrogenase promoter which is induced by ethanol (Nagao, R. T., et al., Miflin, B. J., Ed. Oxford Surveys of Plant Molecular and Cell Biology, Vol. 3, p. 384–438, Oxford University Press, Oxford 1986) or the Lex A promoter which is triggered with chemical treatment and is available through Ligand pharmaceuticals. The inducible promoter may be in an induced state throughout seed formation or at least for a period which corresponds to the transcription of the DNA sequence of the recombinant DNA molecule(s).

OTHER REGULATORY ELEMENTS

In addition to a promoter sequence, an expression cassette or construct should also contain a transcription termination region downstream of the structural gene to provide for efficient termination. The termination region or polyadenylation signal may be obtained from the same gene as the promoter sequence or may be obtained from different genes. Polyadenylation sequences for plant cells include, but are not limited to the *Agrobacterium octopine* synthase signal (Gielen et al., *EMBO J.* (1984) 3:835–846) or the nopaline synthase signal (Depicker et al., *Mol. and Appl. Genet.* (1982) 1:561–573).

MARKER GENES

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed plant. Polymerase chain reactions are also used to identify the presence of a transgene or expression using reverse transcriptase PCR amplification to monitor expression and PCR on genomic DNA. Other commonly used selection markers include the ampicillin resistance gene, the tetracycline resistance and the hygromycin resistance gene. Transformed plant cells thus selected can be induced to differentiate into plant structures which will eventually yield whole plants. It is to be understood that a selection marker gene may also be native to a plant.

TRANSFORMATION

A recombinant DNA molecule may be integrated into the genome of a plant by first introducing a recombinant DNA molecule into a plant cell by any one of a variety of known methods. Preferably the recombinant DNA molecule(s) are inserted into a suitable vector and the vector is used to introduce the recombinant DNA molecule into a plant cell.

The use of Cauliflower Mosaic Virus (CaMV) (Howell, S. H., et al, 1980, *Science*, 208:1265) and gemini viruses (Goodman, R. M., 1981, *J. Gen Virol.* 54:9) as vectors has been suggested but by far the greatest reported successes have been with Agrobacteria sp. (Horsch, R. B., et al, 1985, *Science* 227:1229–1231).

Methods for the use of Agrobacterium based transformation systems have now been described for many different species. Generally strains of bacteria are used that harbor modified versions of the naturally occurring Ti plasmid such that DNA is transferred to the host plant without the subsequent formation of tumors. These methods involve the insertion within the borders of the Ti plasmid the DNA to be inserted into the plant genome linked to a selection marker gene to facilitate selection of transformed cells. Bacteria and plant tissues are cultured together to allow transfer of foreign DNA into plant cells then transformed plants are regenerated on selection media. Any number of different organs and tissues can serve as targets from Agrobacterium mediated transformation as described specifically for members of the Brassicaceae. These include thin cell layers (Charest, P. J., et al, 1988, *Theor. Appl. Genet.* 75:438–444), hypocotyls (DeBlock, M., et al, 1989, *Plant Physiol.* 91:694–701), leaf discs (Feldman, K. A., and Marks, M. D., 1986, *Plant Sci.* 47:63–69), stems (Fry J., et al, 1987, *Plant Cell Repts.* 6:321–325), cotyledons (Moloney M. M., et al, 1989, *Plant Cell Repts.* 8:238–242) and embryoids (Neuhaus, G., et al, 1987, *Theor. Appl. Genet.* 75:30–36), or even whole plants using in vacuum infiltration and floral dip or floral spraying transformation procedures available in Arabidopsis and Medicago at present but likely applicable to other plants in the hear future. It is understood, however, that it may be desirable in some crops to choose a different tissue or method of transformation.

Other methods that have been employed for introducing recombinant molecules into plant cells involve mechanical means such as direct DNA uptake, liposomes, electroporation (Guerche, P. et al, 1987, *Plant Science* 52:111–116) and micro-injection (Neuhaus, G., et al, 1987, *Theor. Appl. Genet.* 75:30–36). The possibility of using microprojectiles and a gun or other device to force small metal particles coated with DNA into cells has also received considerable attention (Klein, T. M. et al., 1987, *Nature* 327:70–73).

It is often desirable to have the DNA sequence in homozygous state which may require more than one transformation event to create a parental line, requiring transformation with a first and second recombinant DNA molecule both of which encode the same gene product. It is further contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques or PCR-based methods known to those of skill in the art.

The regenerated plants are transferred to standard soil conditions and cultivated in a conventional manner. After the expression or inhibition cassette is stably incorporated into regenerated transgenic plants, it can be transferred to other plants by sexual crossing. Any of a number of standard breeding techniques can be used, depending upon the species to be crossed.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

As indicated above, it may be desirable to produce plant lines which are homozygous for a particular gene. In some species this is accomplished rather easily by the use of anther culture or isolated microspore culture. This is especially true for the oil seed crop Brassica napus (Keller and Armstrong, Z. flanzenzucht 80:100–108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Creation of homozygous parental lines makes possible the production of hybrid plants and seeds which will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The following examples serve to better illustrate the invention described herein and are not intended to limit the invention in any way. All references cited herein are hereby expressly incorporated to this document in their entirety by reference.

EXAMPLES

Cells, Viruses, and Insects. The *Spodoptera frugiperda* Smith Sf9 cell line (Vaughn, J. L., et al., 1977. The establishment of two cell lines from the insect *Spodoptera frugiperda* (Lepidoptera; Noctuidae). In Vitro 13, 213–217) was maintained in TNM-FH medium (JRH Biosciences, Lenexa, KS) supplemented with 3% fetal bovine serum (Intergen, Purchase, NY), antibiotics (1 U/ml penicillin, 1 µg/ml streptomycin; Sigma, St. Louis, Mo.), and 0.1% Pluronic F-68 (JRH Biosciences). *Trichoplusia ni* Hübner *BTI-TN*-5B1–4 ("High Five"; Wickham, T. J., et al., 1992.Screening of insect cell lines for the production of recombinant proteins and infectious virus in the baculovirus expression system. *Biotechnol. Prog.* 8, 391–396) cells were maintained in Ex-Cell 405 medium (JRH Biosciences) supplemented with antibiotics.

The wild-type AcMNPV strain C6 (Possee, R. D. 1986. Cell-surface expression of influenza virus haemagglutinin in insect cells using a baculovirus vector. *Virus Res.* 5, 43–59) and the recombinant viruses described in this study were propagated in Sf9 cells and titered by plaque assay. The recombinant viruses AcMLF9. AaIT and AcMLF9. LqhIT2 express the scorpion toxins AaIT and LqhIT2, respectively, from the AcMNPV p6.9 promoter (Harrison and Bonning, 2000, "Use of scorpion neurotoxins to improve the insecticidal activity of Rachiplusia ou multicapsid nucleopolyhedrovirus", *Biol. Control*, 17(2):191–201).

Eggs of *Heliothis virescens* were obtained from the USDA/ARS Southern Insect Management Research Unit in Stoneville, Miss. Larvae were reared on *H. virescens* diet obtained from Southland Products (Lake Village, Ark.) at 27° C. and a 14:10 light:dark cycle.

Construction of Recombinant AcMNPV. Protease genes were cloned into the transfer vectors pAcMLF9 (Harrison and Bonning, 2000, supra) and pAcP(+) IE1TV3 (Jarvis, D. L., et al., 1996. Immediate early baculovirus vectors for foreign gene expression in transformed or infected cells. *Protein Express. Purif.* 8, 191–203). These vectors provide for expression of inserted genes from the promoters of the AcMNPV p6.9 and ie-1 genes, respectively. Both transfer vectors contain an intact polyhedrin gene and provide for the production of occlusion-positive viruses. Three proteases were selected for insertion into AcMNPV:

(1) Rat "activated" stromelysin-1: The stromelysins are a group of matrix (zinc) metalloproteases that degrade a variety of extracellular matrix proteins, including type IV collagen and laminin (Birkedal-Hansen, H. (1995). Proteolytic remodeling of extraceilular matrix. *Curr. Op. Cell Biol.* 7, 728–735). Matrix metalloproteases such as the stromelysins are expressed and secreted as inactive zymogens. A conserved sequence in the propeptides of matrix metalloproteases, PRCG(V/N)PD (SEQ ID NO:1) is involved in maintaining the latency of these enzymes. We obtained a form of the rat stromelysin-1 gene with a mutation in the conserved propeptide sequence (Val92 to Gly) that results in the production of a fully active form of the protease (Park, A. J., et al., 1991. Mutational analysis of the transin (rat stromelysin) autoinhibitor region demonstrates a role for residues surrounding the "cysteine switch". *J. Biol. Chem.* 266, 1584–1590). The coding sequence for this activated form of rat stromelysin-1 was isolated as an EcoR I fragment from pMMTV-STR1-V/G (Witty, J. P., et al., 1995. Matrix metalloproteases are expressed during ductal and alveolar mammary morphogenesis, and misregulation of stromelysin-1 in transgenic mice induces unscheduled alveolar development. *Mol. Biol. Cell* 6, 1287–1303) and cloned into the EcoR I site of pAcMLF9 and the Stu I site of pAcP(+)IE1TV3.

(2) Human gelatinase A; The gelatinases (also known as type IV collagenases) degrade native and denatured collagens and other extracellular matrix proteins (Birkedal-Hansen, 1995, supra). A proline-to-glycine substitution was inserted by site-directed niutagenesis in the conserved matrix metalloprotease propeptide sequence PRCG(V/N)PD (SEQ ID NO 1) at the second, underlined proline (Pro105) of gelatinase A (Collier, I. E., et al., 1988. H-ras oncogene-transformed human bronchial epithelial cells (TBE-1) secrete a single metalloprotease capable of degrading basement membrane collagen. J. Biol. Chem. 263, 6579–6587) using the Transformer Site-Directed Mutageneisis kit from Clontech (Palo Alto, Calif.). The activated gelatinase A coding sequence was then isolated as a Not I—EcoR I fragment and blunt-end ligated into the StuI site of pAcP(+)IE1T1V3 and the BglII site of pAcMLF9.

(3) Cathepsin L from Sarcophaga peregrina: The cysteine protease cathepsin L is normally an intracellular enzyme. However, a cathepsin L from the flesh fly, S. peregrina is constitutively secreted from an embryonic S. peregrina cell line and also secreted from S. peregrina imaginal discs in response to 20-hydroxyecdysone (Homma, K., et al., 1994. Purification, characterization, and cDNA cloning of pro-cathepsin L from the culture medium of NIH-Sape-4, an embryonic cell line of Sarcophaga peregrina (flesh fly), and its involvement in the differentiation of imaginal discs. J. Biol. Chem. 269, 15258–15264.). The secretion and activity of this enzyme correlates with the eversion of imaginal discs during their development into primordial adult leg structures in vitro and the selective degradation of two proteins with apparent molecular weights of 200 and 210 kDa (Homma and Natori, 1996). These proteins are located on the surfaces of imaginal discs and are believed to be BM components. The S. peregrina cathepsin L coding sequence was isolated as a Vsp I fragment from plasmid pKYH5 (Homma et al., 1994, supra) and cloned by blunt-end ligation into the Bgl II site of pAcMLF9 and the Stu I site of pAcP(+)IE1TV3.

The resulting constructs were used to make the occlusion-positive recombinant viruses listed in Table 1 by co-transfection of Sf9 cells with linearized BacPAK6 viral DNA (Kitts, P. A., and Possee, R. D. 1993.A method for producing recombinant baculovirus expression vectors at high frequency. Biotechniques 14, 810–817) using calcium phosphate precipitation (Summers, M. D., and Smith, G. E. 1987. "A Manual of Methods for Baculovirus Vectors and Insect Cell Culture Procedures.". Tex. Agric. Exp. Stn. Bull., 1555). Techniques for selection and plaque-purification of recombinant viruses were as described by Summers and Smith (1987). Recombinant virus clones were checked for correct insertion of foreign sequences by restriction enzyme analysis and polymerase chain reaction amplification and sequencing of the region where the protease genes were inserted.

TABLE 1

Characteristics of baculoviruses used in this study

| Virus | Gene inserted | Promoter used for expression |
|---|---|---|
| AcMNPV-C6 | None (wild-type) | — |
| AcMLF9.AaIT | AaIT scorpion toxin[a] | p6.9 |
| AcMLF9.LqhIT2 | LqhIT2 scorpion toxin[a] | p6.9 |
| AcIE1TV3.STR1 | rat stromelysin-1 | ie-1 |
| AcMLF9.STR1 | rat stromelysin-1 | p6.9 |
| AcIE1TV3.GEL | human gelatinase A | ie-1 |
| AcMLF9.GEL | human gelatinase A | p6.9 |
| AcIE1TV3.ScathL | flesh fly cathepsin L | ie-1 |
| AcMLF9.ScathL | flesh fly cathepsin L | p6.9 |

[a]Harrison and Bonning, 2000

Characterization of expressed protease activity. High Five cells were seeded into 35 mm diameter dishes at a density of $3 \times 10^6$ cells/dish and infected with AcMNPV-C6 and recombinant viruses at a multiplicity of infection (M.O.I.) of 1.At 72 hours post-infection (h p. i.), medium from the infections was harvested and clarified by low-speed centrifugation (500×g for five minutes). For some treatments, medium samples were concentrated by centrifugation through Centricon-30 units (Millipore, Bedford, Mass.).

Protease activity was measured either by zymography or by assay with the chromogenic substrate azocoll (Calbiochem, La Jolla, Calif.). For zymography, samples of medium from cells infected with gelatinase A-expressing viruses were concentrated 3-fold, and samples from cells infected with stromelysin-1-expressing viruses were concentrated 10-fold. Medium from mock- and wild-type virus-infected cells were concentrated 3-fold (for gelatin zymography) or 10-fold (for casein zymography). Aliquots (20 μl) of infected cell culture medium were mixed with equal volumes of 2× non-denaturing protein sample buffer (2% sodium dodecyl sulfate-172 mM Tris-HCl, pH 6.8–28% glycerol-0.2% bromophenol blue) and incubated for 20 min at 37° C. Samples were electrophoresed on 10% polyacrylamide gels that contained either 0.1% gelatin (for analysis of gelatinase A expression) or 0.05% α-casein (for analysis of stromelysin-1 expression). After electrophoresis, the gels were incubated in 2.5% Triton X-100 for one h at room temperature. The gels were rinsed twice with distilled $H_2O$ and incubated 48 h at 37° C. in 50 mM Tris, pH 7.6–10 mM $CaCl_2$-200 mM NaCl-50 μM $ZnSO_4$. The gels were stained with Coomassie blue R-250, and proteases were visualized as clear bands in a blue background.

Azocoll assays were carried out as described by Fisher and Werb (1995). For assays on medium from cells infected with the viruses expressing the mammalian proteases, all medium samples were concentrated 10-fold except for medium from AcMLF9.STR1-infected cells. Samples for analysis of S. peregrina cathepsin L expression were not concentrated. Aliquots of infected cell medium (2.5 μl for AcMLF9. ScathL-infected cells, 40 μl for all other samples) were mixed with 200 μl of 2 mg/ml azocoll suspended either in 50 mM Tris, pH 7.6–10 mM $CaCl_2$-200 mM NaCl-50 μM $ZnSO_4$ (for detection of stromelysin-1 and gelatinase A activity) or in 0.1 M sodium acetate, pH 5.0 (for detection of cathepsin L activity) in a final volume of 240 μl. A control reaction with sufficient dispase (Boehringer Mannheim, Indianapolis, Ind.) to digest all azocoll in the reaction tube was used as a standard. To confirm that azocoll digestion was due to matrix metalloprotease or cysteine protease activity, reactions were set up with 1 mM 1,10-phenanthroline (Sigma), a selective inhibitor of zinc metalloproteases, or 10 μM trans-epoxysuccinyl-L-leucylamido-(4-guanidino)butane (E-64; Sigma), a specific inhibitor of cysteine proteases. Three replicate samples were tested for each treatment, and duplicate reactions were set up for each sample. Reactions were incubated for 17 h at 37° C. Undigested azocoll was pelleted by centrifugation at 2000×g for 10 minutes. Absorbance of the supernatant was measured at 520 nm for each reaction, and mg azocoll digested/ml medium was calculated based on the absorbance of the dispase control reaction (Fisher, S. J., and Werb, Z. 1995. The catabolism of extracellular matrix components. In "Extracellular Matrix: A Practical Approach" (M. A. Haralson, and J. R. Hassell, Eds.), pp. 261–287. Oxford University Press, New York).

Polyhedra production and bioassays. To produce polyhedra for bioassays, H. virescens larvae molting from $4^{th}$ to $5^{th}$ instar were placed individually in ⅝-ounce cups with no diet. After completing the molt to $5^{th}$ instar, the larvae were infected by allowing them to feed upon a small diet cube contaminated with $10^5$ polyhedra derived from infected Sf9 cells. Some of the larvae infected with AcMNPV-C6, AcMLF9.STR1, and AcMLF9.ScathL were dissected and photographed. Polyhedra were isolated from cadavers by a standard method (O'Reilly, D. R., et al., 1992. "Baculovirus Expression Vectors: A Laboratory Manual." Freeman, New York).

Lethal concentration bioassays were conducted using the droplet feeding method of Hughes and Wood (1981) with five different concentrations of occlusions (0.5, 2.0, 5.0, 10.0, and 20.0×10⁵ polyhedra/ml) and 35 neonate larvae/concentration. Mortality was scored at approximately two weeks post-infection, when surviving larvae in each treatment had either pupated or were in the pre-pupal stage. Dose-mortality relationships were analyzed by probit analysis using the POLO program (Russell, R. M., et al., 1977. POLO: A new computer program for probit analysis. *Bull. Entomol. Soc. Am.* 23, 209–213). Comparison of $LC_{50}$s was carried out by the lethal dose ratio comparison method of Robertson and Preisler (1992), "Pesticide Bioassays with Arthropods." CRC Press, Boca Raton, Fla.

Survival time bioassays were prepared by droplet feeding with an $LC_{99}$ dose of virus. The doses of AcMNPV-C6, AcMLF9.AaIT, AcMLF9.LqhIT2, AcIE1TV3.STR1, AcMLF9.STR1, AcIE1V3.GEL, AcMLF9.GEL, AcIE1TV3.ScathL, and AcMLF9.ScathL used against neonate *H. virescens* were 1.80, 2.38, 4.29, 3.44, 4.29, 4.44, 1.74, 2.6, and 3.37×10⁶ polyhedra/ml, respectively. Mortality was scored every 4–12 h, and larvae were counted as dead when they no longer moved when probed. Median survival times ($ST_{50}$) and 95% confidence limits were calculated using the Kaplan-Meier Estimator (Kalbfleisch and Prentice, 1980) with survivors excluded from the analysis. Comparison of $ST_{50}$s was carried out using the log-rank test (Kalbfleisch, J. D., and Prentice, R. L. 1980. "The Statistical Analysis of Failure Time Data." Wiley, New York). In addition to survival time bioassays carried out with individual viruses, bioassays also were conducted with combinations of protease viruses and AcMLF9.LqhIT2. In this case, the infections were carried out with an $LC_{99}$ dose of each virus to obtain a final dose of 2× $LC_{99}$. All bioassays were repeated at least three times over the course of six months.

To measure feeding damage caused by virus-infected larvae, *H. virescens* 2$^{nd}$ instar larvae were starved overnight and were mock-infected or infected with a 5× neonate $LC_{99}$ dose of AcMNPV-C6, AcMLF9.LqhIT2, and AcMLF9.ScathL by the droplet feeding method. These doses resulted in 100% mortality by the end of the bioassay. Infected and mock-infected larvae were transferred individually to 35 mm and 60 mm diameter dishes, respectively, containing pieces of iceberg lettuce on damp filter paper. Lettuce pieces were replaced every 2 to 3 days. The areas of the lettuce pieces were measured with a LI-COR 3100 area meter (LI-COR Inc., Lincoln, Nebr.) before and after feeding. After six days, all virus-infected larvae were dead, and the total area consumed by each larva was determined. Results were analyzed by Kruskal-Wallis ANOVA followed by Dunn's test. Feeding damage assays were repeated three times.

All recombinant viruses encoding proteases (Table 1) produced extracellular protease activity above levels observed in medium from mock or wild-type virus infections. In casein zymographs, two bands migrating between the 45 and 66 kDa markers were observed with medium from cells infected with stromelysin-1 expressing viruses, but not with medium from wild-type or mock-infected cells (FIG. 1A). This result is consistent with the observed mobility of stromelysin-1, which normally migrates as a doublet at 57 and 59 kDa in SDS-PAGE (Galazka, G., et al., 1996. APMA (4-aminophenylmercuric acetate) activation of stromelysin-1 involves protein interactions in addition to those with cysteine-75 in the propeptide. *Biochemistry* 35, 11221–11227). Other bands migrating between the 31 and 45 kDa markers were also observed. Some of these bands were present in the mock and wild-type virus samples, while others were assumed to be proteolytic fragments derived from stromelysin-1. Gelatin zymographs showed a band co-migrating with the 66 kDa marker and with purified human gelatinase A in medium from gelatinase A-expressing viruses, but not in the mock-infected and wild-type virus-infected medium (FIG. 1B). Fragments of purified human gelatinase A resulting from autodegradation were also visible. For both stromelysin-1 and gelatinase A, viruses utilizing the p6.9 promoter to drive expression produced more protease than viruses utilizing the ie-1 promoter. The *S. peregrina* cathepsin L was not detected by zymography under any of the conditions tested.

Figure 2:
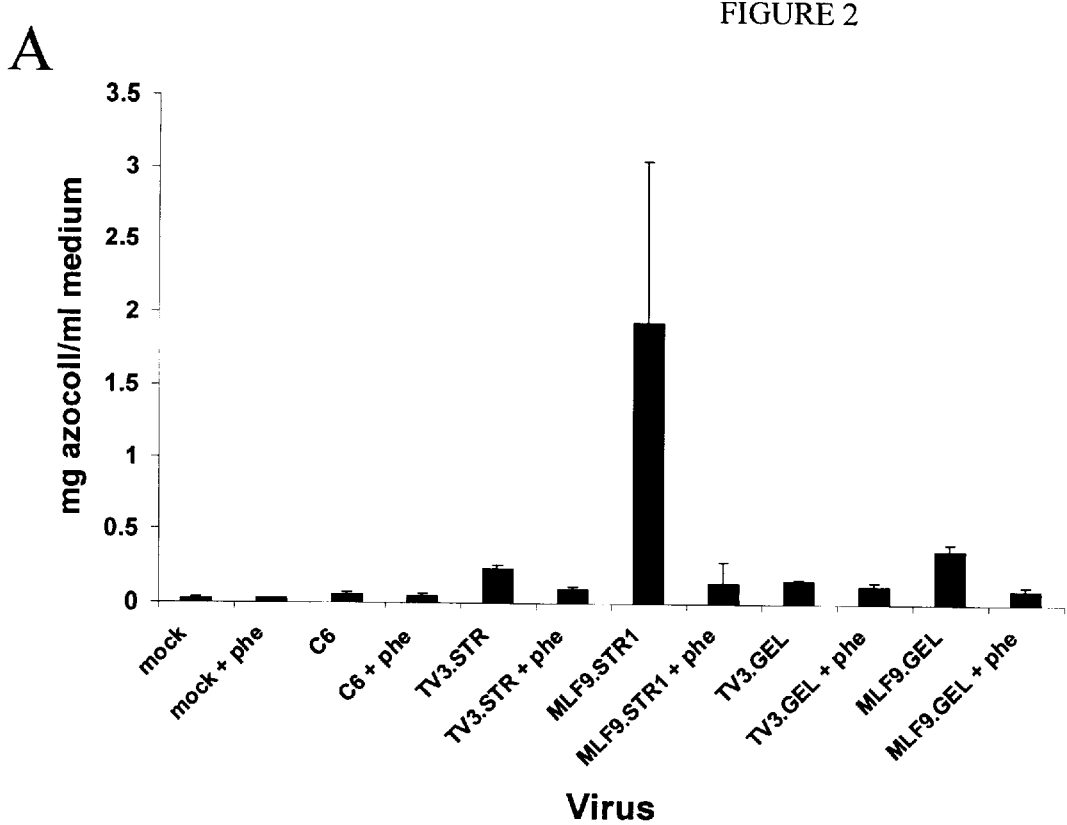
FIG. 2. Detection of proteolytic activity in the medium of infected and uninfected High Five cells by azocoll assay. (A) Azocoll assays carried out at pH 7.6 of medium from mock-infected cells (mock) and cells infected with wild-type AcMNPV (C6) or recombinant AcMNPV expressing rat stromelysin-1 (TV3.STR1, MLF9.STR1) or human type IV collagenase (TV3.GEL, MLF9.GEL). (B) Azocoll assays carried out at pH 5.0 of medium from mock-infected cells and cells infected with wild-type AcMNPV and recombinant AcMNPV expressing *S. peregrina* cathepsin L (TV3.ScathL, MLF9.ScathL). For each treatment, a duplicate set of reactions were set up with 1 mM 1,10-phenanthroline (phe) or 10 $\mu$M trans-epoxysuccinyl-L-leucylamido-(4-guanidino)butane (E-64). The means of three replicates with 1 standard deviation are shown.
Figure 2:
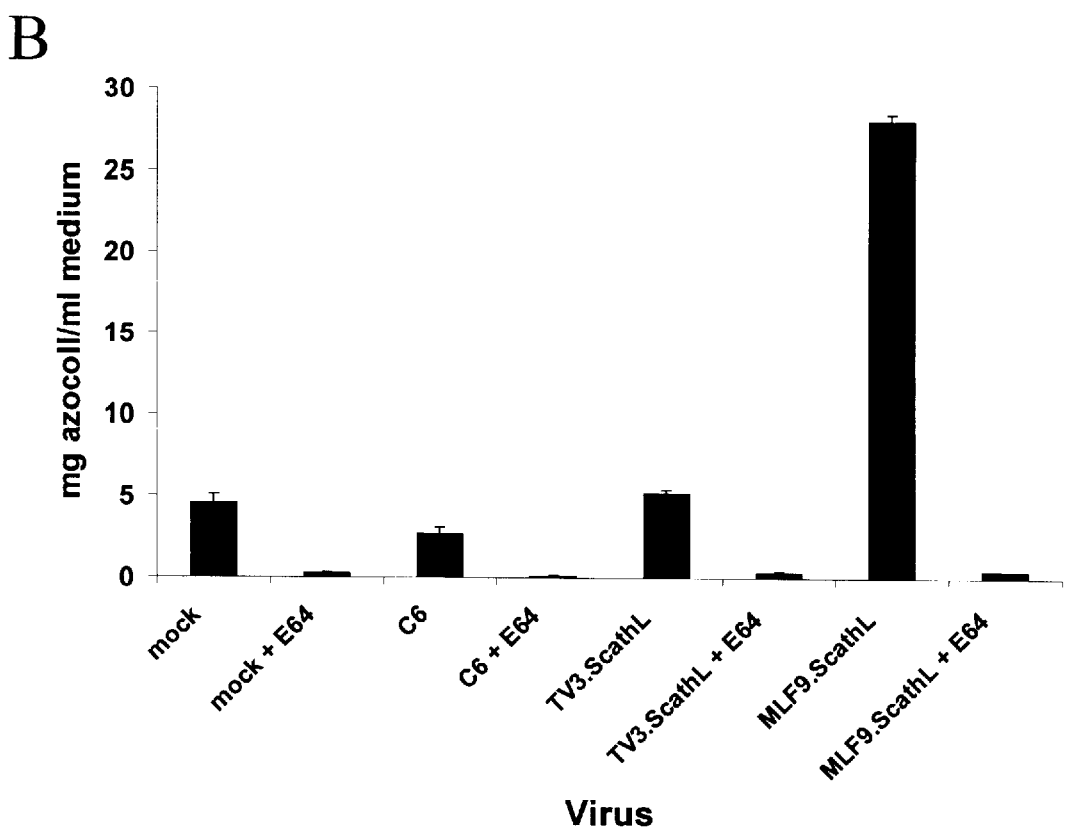

In azocoll assays, proteolytic activity was detected in the supernatants from cells infected with the stromelysin-and gelatinase-expressing viruses (FIG. 2A). This activity was inhibited by 1,10-phenanthroline, indicating that it was due to a zinc metalloprotease. As with the zymography experiments, less activity was present in medium from cells infected with viruses that utilized the ie-1 promoter to drive protease expression than that obtained with the p6.9 promoter. In medium from cells infected with the cathepsin L-expressing viruses, optimal collagenolytic activity was observed at pH 5.0, with less activity at pH 4.0 and no activity at pH 6.0 (data not shown). Homma et al. (1994), supra, reported that the optimal activity of purified *S. peregrina* cathepsin L was pH 3.0–4.0. With azocoll assays carried out at pH 5.0, a substantial quantity of E-64-inhibitable protease activity was detected in the medium of mock-infected cells (FIG. 2B). Less activity was present in AcMNPV-C6-infected cell medium. The medium of cells infected with AcMLF9.ScathL contained approximately ten-fold more E-64-inhibitable protease activity than that of wild-type-infected cells. Much less activity was present in the medium of AcIE1TV3.ScathL-infected cells, although this virus still produced twice as much activity as wild-type virus-infected cells.

Expression of the three proteases was also detected in the hemolymph of 5$^{th}$ instar *H. virescens* larvae infected with AcMLF9.STR1, AcMLF9.GEL, and AcMLF9.ScathL by either zymography or azocoll assay (data not shown). Titers of budded virus in the medium of Sf9 cells infected with recombinant viruses were indistinguishable from those of AcMNPV-C6, and no obvious reduction in polyhedra production was observed in High Five cells infected with the protease-expressing viruses (data not shown). These observations indicate that the budded and occluded forms of AcMNPV were not degraded by the recombinant proteases.

Figure 3:
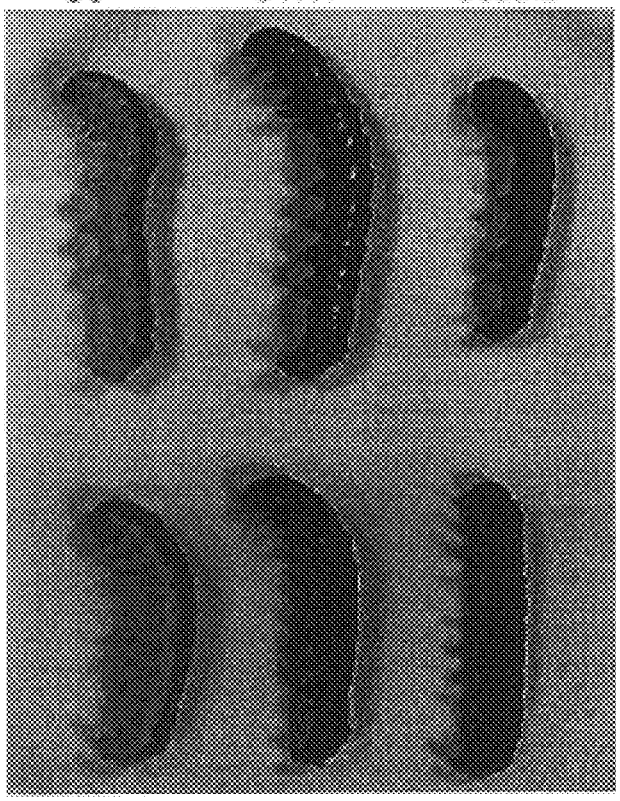
FIG. 3. Cuticular melanization of larvae infected with protease-expressing viruses. Fifth instar *H. virescens* larvae were infected with wild-type AcMNPV-C6 and recombinant AcMNPV expressing rat stromelysin-1 (AcMLF9.STR1) and *S. peregrina* cathepsin L (AcMLF9.ScathL) from the ACMNPV p6.9 promoter. Larvae were photographed at 4 d post-infection.
Figure 4:
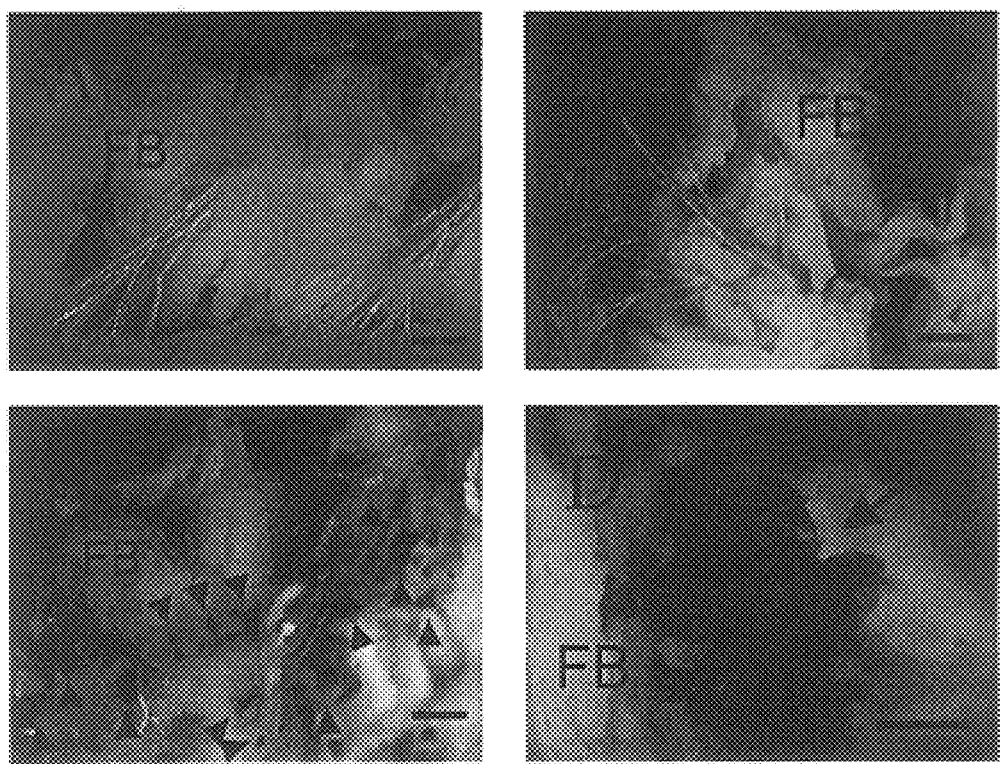
FIG. 4. Internal melanization of larvae infected with protease-expressing viruses. Internal anatomy of $5^{th}$ instar *H. virescens* larvae infected with wild-type AcMNPV-C6 (A), AcMLF9.STR1 (B), and AcMLF9.ScathL (C, D) is displayed. Fat body (FB) and midgut (MG) are labelled. Arrows and arrowheads indicate sites of tissue melanization. Bars: 2 mm (A, B, C), 0.5 mm (D).

Fifth-instar *H. virescens* larvae infected with AcMLF9.ScathL exhibited extensive cuticular melanization by 4 days p. i., often occurring prior to death of the insect (FIG. 3). No wild-type virus-infected larvae displayed cuticular melanization at this time. Larvae infected with AcMLF9.STR1 (FIG. 3) and AcIE1TV3.ScathL (not shown) also exhibited cuticular melanization, but to a lesser extent than that seen with AcMLF9.ScathL-infected larvae. Examination of the internal anatomy of AcMLF9.ScathL-infected 5$^{th}$ instar larvae revealed a variable degree of melanization of tissues (FIG. 4). No internal melanization was observed with AcMNPV-C6- or AcMLF9.STR1-infected larvae. No melanization of hemolymph was observed in larvae infected with any of the viruses, but a considerable amount of fragmentation of tissues was observed in approximately half the larvae infected with AcMLF9.ScathL (not shown).

Lethal concentration bioassays did not reveal any statistically significant differences among the $LC_{50}$ values for AcMNPV-C6 and the recombinant viruses (Table 2).

TABLE 2

Dose-Mortality Response of Neonate Larvae Infected with Wild-Type and Recombinant *Autographa californica* nucleopolyhedroviruses[a]

| Virus | $LC_{50}{}^{b} \times 10^5$ (95% CL) | Slope (±SE) | Heterogeneity |
|---|---|---|---|
| AcMNPV-C6 | 0.77a (0.46–1.16) | 1.29 (±.194) | 0.91 |
| AcIE1TV3.ScathL | 1.19a (0.82–1.65) | 1.74 (±.224) | 0.58 |
| AcMLF9.ScathL | 0.69a (0.43–1.01) | 1.51 (±.217) | 0.94 |
| AcMNPV-C6 | 0.89a (0.54–1.32) | 1.85 (±.282) | 0.26 |
| AcIE1TV3.STR1 | 0.89a (0.45–1.38) | 1.70 (±.302) | 0.93 |
| AcMLF9.STR1 | 0.54a (0.31–0.81) | 1.79 (±.296) | 0.38 |
| AcMNPV-C6 | 0.70a (0.27–1.33) | 1.79 (±.257) | 1.27 |
| AcIE1TV3.GEL | 0.65a (0.38–0.97) | 1.43 (±.221) | 0.51 |
| AcMLF9.GEL | 0.58a (0.23–1.08) | 1.83 (±.264) | 1.23 |

[a]Bioassays with recombinant baculoviruses expressing different proteases were conducted separately
[b]Polyhedra/ml, calculated with the POLO probit analysis program (Russell et al., 1977) and reported with 95% confidence limits (95% CL). For each set of treatments, values with different letters are significantly different at $P < 0.05$.

However, the median survival time of larvae infected with AcMLF9.ScathL was significantly lower than those infected with AcMNPV-C6 and the toxin-expressing viruses AcMLF9.AaIT and AcMLF9.LqhIT2 (Table 3). AcMLF9.GEL killed larvae slightly but significantly faster than AcMNPV-C6 in two out of three trials. No significant reduction in survival time was observed with larvae infected with any of the other protease-expressing viruses, including AcIE1TV3.ScathL.

TABLE 3

Time-Mortality Response of Neonate Larvae Infected with Wild-Type and Recombinant *Autographa californica* nucleopolyhedroviruses

| Viruses | $ST_{50}$ (h p.i.) | 95% CL |
|---|---|---|
| Infection with a single virus[a] | | |
| AcMNPV-C6 | 98.0 a | 91.0–103.5 |
| AcMLF9.AaIT | 73.5 b | 66.5–78.5 |
| AcMLF9.LqhIT2 | 66.0 c | 59.5–66.0 |
| AcIE1TV3.STR1 | 95.0 a | 88.0–100.5 |
| AcMLF9.STR1 | 99.5 a | 94.0–111.0 |
| AcIE1TV3.GEL | 94.0 ad | 87.0–94.0 |
| AcMLF9.GEL | 86.5 d | 86.5–94.0 |
| AcIE1TV3.ScathL | 92.5 a | 89.0–96.0 |
| AcMLF9.ScathL | 48.0 e | 48.0–48.0 |
| Mixed infections[b] | | |
| AcMNPV-C6 (2X $LC_{99}$ dose) | 97.5 a | 90.0–97.5 |
| AcMLF9.LqhIT2 + C6 | 62.5 b | 59.0–66.0 |
| AcMLF9.ScathL + C6 | 34.0 c | 34.0–49.0 |
| AcIE1TV3.STR1 + Lq | 64.0 b | 57.5–64.0 |
| AcMLF9.STR1 + Lq | 64.0 b | 57.5–64.0 |
| AcIE1TV3.GEL + Lq | 63.0 b | 56.5–63.0 |
| AcMLF9.GEL + Lq | 63.0 b | 56.0–69.5 |
| AcIE1TV3.ScathL + Lq | 64.5 b | 57.5–64.5 |
| AcMLF9.ScathL + Lq | 47.5 c | 47.5–52.5 |

[a]Median survival time of insects infected with an $LC_{99}$ dose, determined by the Kaplan-Meier Estimator and reported with 95% confidence limits (95% CL). For each treatment, values with different letters are significantly different at $P < 0.05$. h p.i. = h post infection.
[b]Larvae were infected with an $LC_{99}$ dose of each of two different viruses. C6 = AcMNPV-C6, Lq = AcMLF9.LqhIT2.

To determine if an additive or synergistic effect on survival time could be achieved by simultaneous infection with viruses expressing a BM-degrading protease and a scorpion toxin, survival time bioassays were set up with larvae infected with an $LC_{99}$ dose of each kind of virus. Regardless of the viruses used in each treatment, larvae in these bioassays died with an $ST_{50}$ equivalent to that achieved in dual infections with either AcMLF9.ScathL or AcMLF9.LqhIT2 together with AcMNPV-C6 (Table 3). These data indicate that no additive or synergistic effect on survival time was obtained with any combination of protease- and toxin-expressing viruses.

To measure the effect of Sarcophaga cathepsin L expression on feeding damage caused by virus-infected larvae, the amount of lettuce consumed by $2^{nd}$ instar *H. virescens* infected with AcMNPV-C6, AcMLF9.LqhIT2, and AcMLF9.ScathL was measured and compared. Wild-type virus-infected larvae consumed significantly more lettuce than larvae infected with either AcMLF9.ScathL or AcMLF9.LqhIT2 (Table 4). No significant difference in the leaf area consumed was detected with larvae infected with AcMLF9.LqhIT2 or AcMLF9.ScathL.

TABLE 4

Amount of lettuce consumed by $2^{nd}$ instar *H. virescens* infected with wild-type and recombinant *Autographa californica* nucleopolyhedroviruses

| Treatment | n | Median area[a], cm$^2$ | 25%–75% |
|---|---|---|---|
| Mock | 30 | 29.27 a | 24.886–32.964 |
| AcMNPV-C6 | 30 | 5.21 b | 3.383–6.53 |
| AcMLF9.LqhIT2 | 30 | 0.91 c | 0.515–1.271 |
| AcMLF9.ScathL | 30 | 1.1 c | 0.858–1.608 |

[a]For each treatment, values with different letters are significantly different at $P < 0.05$. $25^{th}$ and $75^{th}$ percentiles are shown.

DISCUSSION

Applicant's original hypothesis was that expression of BM-degrading proteases would hasten the death of baculovirus-infected larvae by accelerating the spread of secondary infection to the host's tissues. Of the protease-expressing AcMNPV that were constructed and tested, AcMLF9.ScathL (expressing *S. peregrina* cathepsin L from the p6.9 promoter) killed *H. virescens* larvae faster than both wild-type AcMNPV and AcMNPV that expressed scorpion toxins. Although *S. peregrina* cathepsin L appears to be involved in digesting basement membrane proteins in *S. peregrina*, the mechanism by which it reduces the survival time of infected *H. virescens* remains to be determined. The melanization of larvae infected with AcMLF9.ScathL suggests that the reduction in survival time may be connected to the inappropriate activation of prophenoloxidase, which is the key enzyme involved in the formation of melanin during wound healing and the immune response in insects. *S. peregrina* cathepsin L may activate the phenoloxidase system directly by either activating the serine protease cascade that leads to the conversion of inactive prophenoloxidase to its active form or by directly activating prophenoloxidase itself. Alternatively, the melanization observed may be a consequence of damage to the basement membranes by the recombinant cathepsin L. In the fruit fly *Drosophila melanogaster* Meigen, tissues with damaged or missing basement membranes undergo melanotic encapsulation (Rizki, R. M., and Rizki, T. M. 1980. Hemocyte responses to implanted tissues in *Drosophila melanogaster* larvae. *Roux's Archives of Developmental Biology* 189, 207–213; Rizki, et al., 1983. *Drosophila* larval fat body surfaces: Changes in transplant compatibility during development. *Roux's Arch. Dev. Biol.* 192, 1–7). The tissue fragmentation observed in AcMLF9.ScathL-infected larvae is also consistent with disruption of the BM. Apart from facilitating the spread of infection to other tissues, damage to BMs may itself result in the death of the insect, possibly by deregulating the ionic and molecular traffic between the hemocoel and tissues.

Although AcMLF9.ScathL killed insects rapidly, AcIE1TV3.ScathL, a virus that expresses the same protease from the ie-1 promoter, did not exhibit any improvement in speed of kill. The AcMNPV ie-1 promoter is weaker than the late p6.9 promoter, but it is activated immediately after infection. We hypothesized that early expression and secretion of proteases may result in sufficient BM solubilization or perforation to allow the first progeny virus emerging from infected midgut cells to immediately penetrate through the BMs surrounding the midgut sheath, enter the hemocoel of the host, and infect hemocytes. Also, Jarvis, D. L., et al., 1996. Immediate early baculovirus vectors for foreign gene expression in transformed or infected cells. *Protein Express. Purif.* 8, 191–203, demonstrated that ie-1 promoter-based expression vectors can produce as much or more of a biologically active secretory pathway protein than conventional baculovirus expression vectors that rely on the polyhedrin (polh) promoter. However, for all three proteases that we expressed in AcMNPV, the p6.9 promoter appeared to drive significantly higher levels of expression and secretion. It is likely that AcIE1TV3.ScathL simply did not produce sufficient cathepsin L to have an effect on the infected host.

With the exception of a minor reduction in survival time with AcMLF9.GEL, viruses expressing the mammalian proteases did not exhibit any discernible improvement in insecticidal properties. This result may be because the protease expressed and secreted by these viruses was at relatively low levels (compare FIG. 2A to FIG. 2B). Alternatively, the mammalian proteases may have failed to bind and digest insect BM proteins. The mammalian proteases also may not have been active within *H. virescens* larvae. *S. peregrina* cathepsin L is normally active at an acid pH. The pH between cells and the surrounding BMs may be sufficiently low for *S. peregrina* cathepsin L activity but may inhibit the two mammalian proteases.

If *S. peregrina* cathepsin L expressed from infected host cells damages the BM and facilitates secondary infection, then in a dual infection of larvae with AcMLF9.ScathL and another virus, both viruses may be able to disseminate within the host more rapidly and establish a more widespread infection of other tissues. If the second virus encodes a toxin, larger quantities of that toxin may be expressed sooner after infection, which may further reduce host survival time. Hence, one would expect to see a synergistic or additive effect on host survival time arising from a dual infection with a protease-expressing virus and a toxin-expressing virus. We did not see any such effect in dual infections with AcMLF9.ScathL and AcMLF9.LqhIT2. The site of action for scorpion toxins is the voltage-gated sodium channels of nervous tissue. Herrmann, R., et al., 1990. The tolerance of lepidopterous larvae to an insect selective neurotoxin. *Insect Biochem.* 20, 625–637 reported that the intact ventral nerve cord and motor nerves of *Spodoptera littoralis* Boisduval were not labelled by [$^{125}$I]AaIT injected into larvae, while desheathed neuronal tissue was specifically labelled. The authors speculated that the coverage of nerves with glial cells may present an impermeable barrier to scorpion toxins. By infecting and migrating through the tracheae, baculoviruses may be capable of bypassing the glial cell coverage and expressing scorpion toxins in sites where the toxins have greater access to the nerves. Hence, simply increasing the concentration of toxin within the hemocoel by enhancing systemic infection via BM disruption may not result in increased access of toxins to sodium channels. Dual infections with AcMLF9.ScathL and a virus expressing another class of insecticidal agent (such as mutated juvenile hormone esterase, EC 3.1.1.1; Bonning, B. C., et al., 1997. Disruption of lysosomal targeting is associated with insecticidal potency of juvenile hormone esterase. *Proc. Natl. Acad. Sci. USA* 94, 6007–6012; Bonning, B. C., et al., 1999. Insecticidal efficacy of a recombinant baculovirus expressing JHE-KK, a modified juvenile hormone esterase. *J. Invertebr. Pathol.* 73, 234–236) may yield the synergistic or additive reduction in survival time that we failed to see with dual infections involving expression of a scorpion toxin.

The use of viruses expressing proteases will be less likely to provoke public anxiety than viruses expressing scorpion toxins. Proteases that target only insect proteins would provide an additional level of safety. Open reading frames (ORFs) with sequence similarity to mammalian matrix metalloproteases recently have been reported in the genomes of a granulovirus (Hayakawa, T., et al., 1999.Sequence analysis of the Xestia c-nigrum granulovirus genome. *Virology* 262, 277–297) and an entomopoxvirus (Afonso, C. L., et al., 1999. The genome of *Melanoplus sanguinipes* entomopoxvirus. *J. Virol.* 73, 533–552). It is unclear what function the polypeptides specified by these ORFs may have in the baculovirus or entomopoxvirus life cycle, although they may accelerate systemic infection by destroying the host BM. Insect- or insect virus-derived proteases may augment insecticidal activity of baculoviruses to a larger extent than proteases derived from other organisms.

What is claimed is:

1. A method for protecting a plant from damage caused by an insect feeding on said plant comprising introducing to said insect via a recombinant baculovirus on said plant, a composition comprising a basement membrane degrading protease wherein said protease is a cathepsin L protease from the flesh fly *Sarcophaga peregrine* encoded by an expressible heterologous polynucleotide contained within said recombinant baculovirus, whereby said protease is expressed and said baculovirus infects said feeding insect, and wherein said protease contacts and degrades a basement membrane of said insect and inhibits the insect feeding on said plant, thereby protecting said plant.

2. The method of claim 1, wherein the heterologous polynucleotide, contained within said baculovirus, is operably linked to a promoter capable of directing expression of said heterologous polynucleotide in an infected cell of said insect.

3. The method of claim 2, wherein said promoter includes a baculovirus promoter selected from the group consisting of p6.9 and ie-1.

* * * * *

SEQUENCE LISTING

<160> NUMBER OF SEQ ID NOS: 1

<210> SEQ ID NO 1
<211> LENGTH: 7
<212> TYPE: PRT

-continued

```
<213> ORGANISM: Homo sapiens
<220> FEATURE:
<221> NAME/KEY: MISC_FEATURE
<222> LOCATION: (1)..(7)
<223> OTHER INFORMATION: X is V or N

<400> SEQUENCE: 1

Pro Arg Cys Gly Xaa Pro Asp
1               5
```